(12) United States Patent
Aoki et al.

(10) Patent No.: US 7,459,447 B2
(45) Date of Patent: Dec. 2, 2008

(54) METHOD FOR TREATING HYPERLIPIDEMIA

(75) Inventors: Taro Aoki, Tokorozawa (JP); Hiroyuki Yamazaki, Higashimurayama (JP); Takashi Maejima, Higashimurayama (JP)

(73) Assignees: Kowa Co., Ltd., Nagoya-shi (JP); Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 11/546,248

(22) Filed: Oct. 12, 2006

(65) Prior Publication Data

US 2007/0032467 A1 Feb. 8, 2007

Related U.S. Application Data

(63) Continuation of application No. 10/997,878, filed on Nov. 29, 2004, now abandoned.

(60) Provisional application No. 60/605,525, filed on Aug. 31, 2004.

(51) Int. Cl.
*A61K 31/397* (2006.01)
*A61K 31/47* (2006.01)
(52) U.S. Cl. .................... 514/210.02; 514/311
(58) Field of Classification Search ............... None
See application file for complete search history.

(56) References Cited

U.S. PATENT DOCUMENTS

| 5,011,930 | A | 4/1991 | Fujikawa et al. |
| 5,102,888 | A | 4/1992 | Fujikawa et al. |
| 5,185,328 | A | 2/1993 | Fukikawa et al. |
| 5,661,145 | A | 8/1997 | Davis |
| 5,854,259 | A | 12/1998 | Fujikawa et al. |
| 5,856,336 | A | 1/1999 | Fujikawa et al. |
| 5,872,130 | A | 2/1999 | Fujikawa et al. |
| 6,465,477 | B1 | 10/2002 | Muramatsu et al. |
| 6,777,552 | B2 | 8/2004 | Niddam-Hildesheim et al. |
| 2004/0126423 | A1 | 7/2004 | Moore et al. |
| 2004/0254120 | A1 | 12/2004 | Fogelman et al. |

FOREIGN PATENT DOCUMENTS

| JP | 8-505141 | 6/1996 |
| WO | WO 95/08532 | 3/1995 |

OTHER PUBLICATIONS

Harry R. Davis Jr. et al., "The Synergistic Hypocholesterolemic Activity of the Potent Cholesterol Absorption Inhibitor, Ezetimibe. In Combination With 3-Hydroxy-3-Methylglutaryl Coenzyme A Reductase Inhibitors in Dogs", Metabolism, vol. 50, No. 10, Oct. 2001, pp. 1234-1241.

*Primary Examiner*—Raymond J Henley, III
(74) *Attorney, Agent, or Firm*—Oblon, Spivak, McClelland, Maier & Neustadt, P.C.

(57) ABSTRACT

Provided is a method for treating hyperlipidemia or hypercholesterolemia, which comprises administering effective doses of ezetimibe and pitavastatin or a salt or lactone derivative thereof.

10 Claims, 1 Drawing Sheet

Mean ± standard error n=6 p<0.01, *p<0.001

Mean ± standard error n=6 p<0.05

METHOD FOR TREATING HYPERLIPIDEMIA

CROSS-REFERENCE TO RELATED APPLICATIONS

The present application is a continuation of U.S. application Ser. No. 10/997,878 filed Nov. 29, 2004, abandoned, and claims the benefit of U.S. provisional application No. 60/605,525 filed Aug. 31, 2004.

TECHNICAL FIELD

The present invention relates to a method for treating hyperlipidemia, which exhibits an excellent blood cholesterol-lowering action.

BACKGROUND ART

Hyperlipidemia is a symptom characterized by the abnormal elevation of lipoprotein levels in blood, particularly cholesterol levels in blood. Hyperlipidemia is known to be closely linked to diseases such as arteriosclerosis and myocardial infarction and its treatment is considered extremely important.

There are a variety of drugs available for the treatment hyperlipidemia or hypercholesterolemia. At present, HMG-CoA reductase inhibitors such as lovastatin, simvastatin, pravastatin, fluvastatin, atorvastatin, rosuvastatin and pitavastatin are most commonly used for its treatment. Of these, pitavastatin ((3R,5S,6E)-7-[2-cyclopropyl-4-(4-fluorophenyl)-3-quinolyl]-3,5-dihydroxy-6-heptenoic acid) is known to exhibit a potent HMG-CoA reductase inhibitory action and therefore be useful as an antihyperlipidemic agent (Japanese Patent No. 2569746, U.S. Pat. No. 5,102,888, EP No. 304, 063).

The blood cholesterol level of patients with hyperlipidemia is lowered by the administration of an HMG-CoA reductase inhibitor. Many patients suffering from hyperlipidemia have a higher blood cholesterol level and their blood cholesterol level is not always possible to fully be lowered by the administration of an HMG-CoA reductase inhibitor. In such a case, treatment with an increased dose of an HMG-COA reductase inhibitor is not advisable from the viewpoint of safety.

On the other hand, ezetimibe ((3R,4S)-1-(4-fluorophenyl)-3-[(3S)-3-(4-fluorophenyl)-3-hydroxypropyl]-4-(4-hydroxyphenyl)-2-azetidinone) is known as an antihyperlipidemic agent which inhibits absorption of diet-induced and bile-acid-induced cholesterol in the intestinal tract, thus lowering the blood cholesterol level by a mechanism different from that of the HMG-COA reductase inhibitor (WO95/08532).

The concomitant use of an HMG-CoA reductase inhibitor and ezetimibe was disclosed to be effective for lowering the blood cholesterol level and treatment of atherosclerosis (WO095/08532). The blood cholesterol level lowering action by the coadministration of an HMG-CoA reductase inhibitor and ezetimibe was also reported (Metab. Clin. Exp., 50(10), 1234-1241 (2001)).

The effect brought about by the concomitant use of pitavastatin and ezetimibe on the treatment of hyperlipidemia remains to be seen, however.

DISCLOSURE OF THE INVENTION

An object of the present invention is to provide a method for treating hyperlipidemia and hypercholesterolemia, which has an excellent blood cholesterol lowering action.

With the foregoing in view, the present inventors have carried out an extensive investigation, and found that the concomitant use of pitavastatin and ezetimibe brings about a remarkably excellent blood cholesterol level lowering action, so it is very useful for the treatment of hyperlipidemia and hypercholesterolemia. Thus the present invention has been accomplished.

In one aspect of the present invention, there is thus provided a method for treating hyperlipidemia, which comprises administering effective doses of ezetimibe and pitavastatin or a salt or lactone derivative thereof.

In another aspect of the present invention, there is also provided a method for treating hypercholesterolemia, which comprises administering effective doses of ezetimibe and pitavastatin or a salt or lactone derivative thereof.

The methods for treating hyperlipidemia and hypercholesterolemia according to the present invention are effective for the treatment of hyperlipidemia and hypercholesterolemia in that these exhibit excellent action in lowering blood cholesterol level.

BEST MODE FOR CARRYING OUT THE INVENTION

Figure 1:
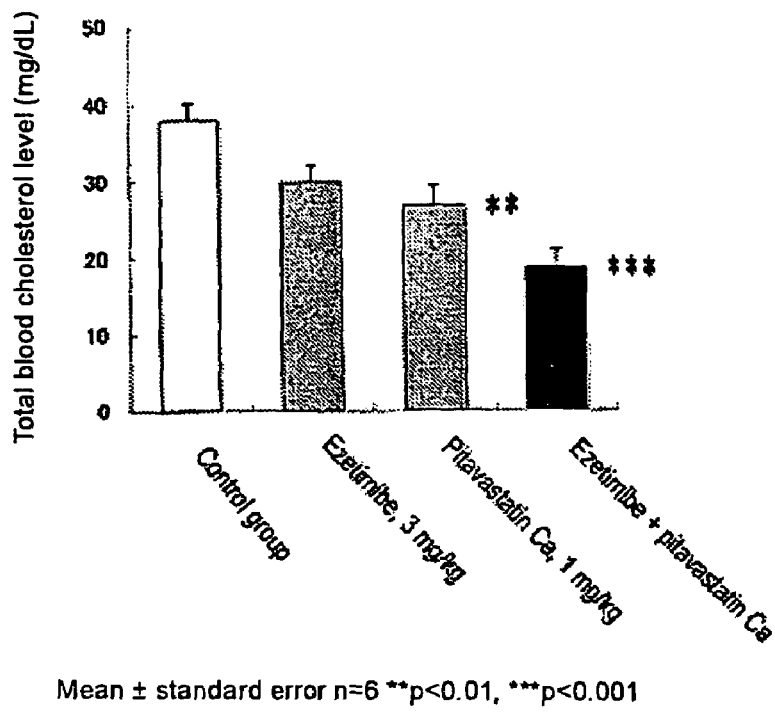
FIG. 1 is a graph showing the blood cholesterol level lowering action brought about by the concomitant use of a calcium salt of pitavastatin and ezetimibe.

Pitavastatin, or salt or lactone derivative thereof (which may hereinafter be called "pitavastatin derivative") to be used in the invention has cholesterol synthesis inhibitory activity based on HMG-CoA reductase inhibition and is known as an antihyperlipidemic agent. Of the pitavastatin derivatives, salts of pitavastatin are preferred, with calcium salt and sodium salt being especially preferred.

Ezetimibe to be used in the invention is known as a medicament exhibiting its effects by inhibiting the cholesterol absorption in the intestine.

According to the present invention, treatment is performed by the coadministration of a pitavastatin derivative and ezetimibe. In the evaluation system using guinea pigs, as will be described later in Examples, the blood cholesterol level is lowered significantly by the concomitant use of the pitavastatin derivative and ezetimibe compared with the single administration of each of them.

In the treatment method of the invention, the dosage form of the pitavastatin derivative and ezetimibe can be selected arbitrarily depending on the purpose of the treatment. Any one of powders, granules, dry syrups, tablets, capsules and injections can be used. Such a dosage form can be prepared by incorporating a pharmaceutically acceptable carrier in the pitavastatin derivative and ezetimibe and adopting a formulation method well known and commonly used in the art.

An orally administrable solid preparation can be obtained by adding an excipient and optionally, a binder, a disintegrant, a lubricant, a coloring agent, a taste corrigent, a smell corrigent and the like, and processing the resulting mixture into tablets, granules, powders or capsules in a conventional manner. As such an additive, those ordinarily accepted in this field can be used. Examples of the excipient include lactose, sodium chloride, glucose, starch, microcrystalline cellulose, and silicic acid; examples of the binder include water, ethanol, propanol, simple syrup, liquefied gelatin, hydroxypropyl cellulose, methyl cellulose, ethyl cellulose, shellac, calcium phosphate, and polyvinylpyrrolidone; examples of the disintegrant include agar powder, sodium hydrogencarbonate, sodium lauryl sulfate, and stearic monoglyceride; examples of the lubricant include purified talc, stearate salt, borax, and polyethylene glycol; examples of the coloring agent include β-carotene, yellow iron sesquioxide, and caramel; and examples of the taste corrigent include sucrose and orange peel.

An orally administrable liquid preparation can be obtained by adding a taste corrigent, a buffer, a stabilizer, a preservative and the like and processing the resulting mixture into an internal medicine, syrup, or elixir in a conventional manner. As such an additive, those ordinarily accepted in this field can be used. Examples of the taste corrigent include sucrose; examples of the buffer include sodium citrate; examples of the stabilizer include tragacanth; and examples of the preservative include paraoxybenzoate ester.

An injection can be obtained by adding a pH regulator, a stabilizer, or an isotonizing agent, and processing the resulting mixture into a subcutaneous injection, an intramuscular injection, or an intravenous injection in a conventional manner. As such an additive, those ordinarily accepted in this field can be used. Examples of the pH regulator include sodium phosphate; examples of the stabilizer include sodium pyrosulfite; and examples of the isotonizing agent include sodium chloride.

No particular limitation is imposed on the using manner of the medicaments in the treatment method of the present invention. Instead of the simultaneous administration, the two medicaments may be administered at certain intervals. In other words, the pitavastatin derivative and ezetimibe may be formulated into one medicament or they may be formulated into respective medicaments but provided as a set. When they are formulated into respective medicaments, their dosage forms are not necessarily the same.

The dosage of these medicaments in the treatment method of the invention is selected arbitrarily depending on the condition of the patient. The pitavastatin derivative may be administered in an amount of from 0.1 to 50 mg, preferably from 1 to 20 mg a day, while ezetimibe may be administered in an amount of from 0.1 to 500 mg, preferably from 1 to 100 mg a day. The administration may be performed once a day or plural times a day.

EXAMPLES

The present invention will next be described in more detail by Examples. It should be borne in mind that the present invention is not limited to or by them.

Example 1

Blood Cholesterol Level Lowering Effect Brought about by the Concomitant Use of Pitavastatin Calcium Salt and Ezetimibe The blood cholesterol level lowering effect when a calcium salt of pitavastatin and ezetimibe were coadministered was measured by the below-described testing method. For comparison, a calcium salt of atorvastatin was used instead of the calcium salt of pitavastatin and the effect brought about by the concomitant use of two medicaments was measured in a similar manner.

1. Animals Provided for the Test and Their Breeding Environment

Six-week-old Hartley male guinea pigs (purchased from Nippon SLC) were provided for the test. Throughout the test period, they were bred in a breeding room maintained at a light-dark cycle (a light term by a room light: from 7:00 am to 7:00 pm), a temperature of 23 ±3° C. and a humidity of 55 ±15% and fed with a solid feedstuff ("RC-4", product of Oriental Yeast Industry) and tap water ad libitum.

2. Preparation of Medicament

Treatment method according to the invention: The calcium salt of pitavastatin and ezetimibe were suspended in a 0.5 wt. % aqueous solution of carboxymethylcellulose sodium (product of Iwai Chemicals Company) and their concentrations were adjusted to 1 mg/mL and 3 mg/mL, respectively. Since the calcium salt of pitavastatin contained 9.43 wt. % of water, 1.1 times the weight of the dosage was weighed for correction. The suspension was refrigerated (4° C.) in a light resistant bottle and adjustment was conducted every 7 days.

Treatment method for comparison: In a similar manner to that described above except the use of the calcium salt of atorvastatin instead of the calcium salt of pitavastatin, a medicament (atorvastatin calcium 5 mg/mL) for comparison test was prepared.

3. Testing Method

The treatment method according to the present invention: Twenty four guinea pigs were classified into four groups (each consisting of 6 guinea pigs), that is, a control group, a single administration group of pitavastatin calcium salt (1 mg/kg), a single administration group of ezetimibe (3 mg/kg), and a coadministration group of pitavastatin calcium salt (1 mg/kg) and ezetimibe (3 mg/kg) so that they differ little in the total blood cholesterol level and blood triglyceride level. These two medicaments were each administered at a dose of 1 mL/kg once a day and this administration was repeated for 14 days. To the control group, a 0.5 wt. % aqueous solution (1 mL/kg) of carboxymethylcellulose sodium was orally administered. In each group, the guinea pigs were fasted for 18 hours after the final administration and then the blood was collected from them to measure the blood cholesterol level.

Treatment method for comparison: twenty four guinea pigs were tested in a similar manner to the method according to the invention. The dosage of the calcium salt of atorvastatin was 5 mg/kg in each of the group nourished by the single use of atorvastatin calcium salt and the group nourished by the concomitant use of atorvastatin calcium salt and ezetimibe.

4. Static Analysis and Data Processing Method

Multigroup comparison between the control group and the medicament administered group was performed using Bartlett's variance analysis—Dunnett's multiple comparative assay. A difference with a significance level less than 5% was regarded as significant.

5. Results

Figure 2:
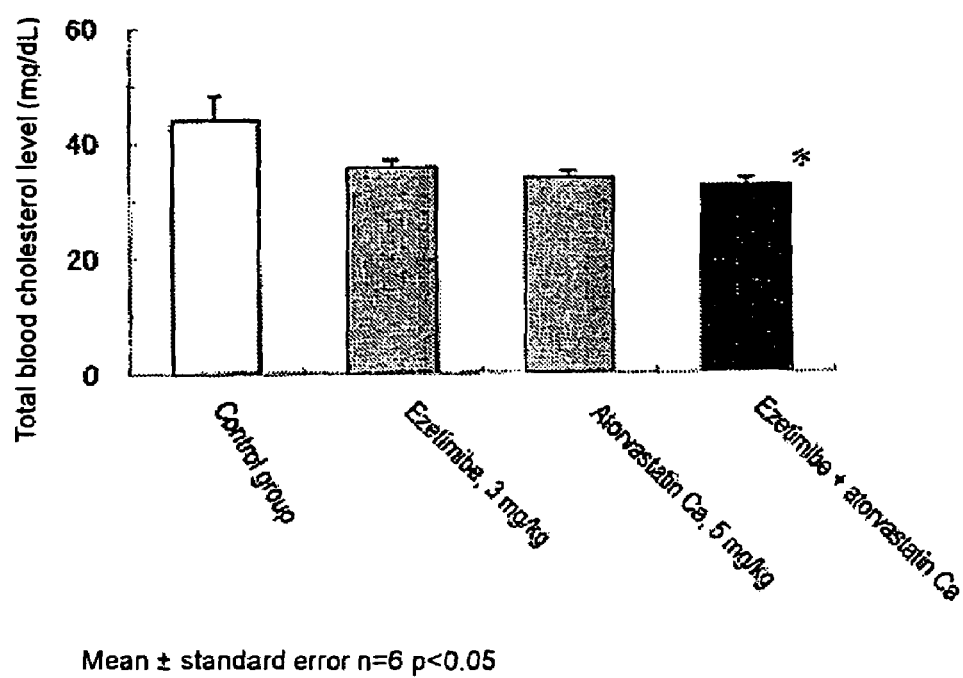
FIG. 2 is a graph showing the blood cholesterol level lowering action brought about by the concomitant use of a calcium salt of atorvastatin and ezetimibe.

The measurement results are shown in Tables 1 and 2, and FIGS. 1 and 2.

A reduction ratio (%) is a value represented by ((total blood cholesterol level of control group on average−total blood cholesterol level of each group on average)/(total blood cholesterol level of control group on average))×100, while a relative index is a value represented by (total blood cholesterol level of each group on average)/(total blood cholesterol level of control group on average).

TABLE 1

Reduction ratio (%) of blood cholesterol level

| Administered group | Reduction ratio | Relative index |
| --- | --- | --- |
| Control group | 0 | 1.0 |
| Group of the single use of ezetimibe | 21 | 0.79 |

TABLE 1-continued

Reduction ratio (%) of blood cholesterol level

| Administered group | Reduction ratio | Relative index |
|---|---|---|
| Group of the single use of pitavastatin Ca | 29 | 0.71 |
| Group of the concomitant use of pitavastatin Ca/ezetimibe | 51 | 0.49 |

TABLE 2

Reduction ratio (%) of blood cholesterol level

| Administered group | Reduction ratio | Relative index |
|---|---|---|
| Control group | 0 | 1.0 |
| Group of the single use of ezetimibe | 19 | 0.81 |
| Group of the single use of atorvastatin Ca | 23 | 0.77 |
| Group of the concomitant use of atorvastatin Ca/ezetimibe | 26 | 0.74 |

In the group of the concomitant use of pitavastatin calcium salt and ezetimibe according to the method of the invention, the blood cholesterol level lowering action was enhanced greatly ($p<0.001$) compared with that of the group of the single use of each medicament. Its effect was synergistic (relative index of the group of concomitant use (0.49)<product (0.56) of relative indices of the groups of single use).

In the treatment method for comparison by using the atorvastatin calcium salt having the most potent blood cholesterol level lowering action among the HMG-CoA reductase inhibitors, on the other hand, the blood cholesterol level lowering action of the group of the concomitant use of atorvastatin calcium salt and ezetimibe was enhanced compared with that of each of the groups of single use, but its effect was additive (relative index (0.74) of the group of concomitant use (0.74)>product (0.62) of refractive indices of the groups of single use).

The concomitant use of the pitavastatin calcium salt and ezetimibe according to the invention has a remarkable blood cholesterol level lowering effect, compared with that of the concomitant use of another HMG-CoA reductase inhibitor and ezetimibe.

The invention claimed is:

1. A method for lowering cholesterol, which comprises administering to a patient in need thereof effective doses of ezetimibe and calcium pitavastatin.

2. A method for lowering cholesterol, which comprises administering to a patient in need thereof from 1 to 100 mg a day of ezetimibe and from 1 to 20 mg a day of calcium pitavastatin.

3. The method of claim 1, wherein ezetimibe and calcium pitavastatin are orally administered.

4. The method of claim 2, wherein ezetimibe and calcium pitavastatin are orally administered.

5. The method of claim 1, wherein ezetimibe and calcium pitavastatin are injected.

6. The method of claim 2, wherein ezetimibe and calcium pitavastatin are injected.

7. The method of claim 1, wherein ezetimibe and calcium pitavastatin are administered simultaneously.

8. The method of claim 2, wherein ezetimibe and calcium pitavastatin are administered simultaneously.

9. The method of claim 1, wherein ezetimibe and calcium pitavastatin are administered separately.

10. The method of claim 2, wherein ezetimibe and calcium pitavastatin are administered separately.

* * * * *